(12) United States Patent
Perez Andres et al.

(10) Patent No.: US 7,745,628 B2
(45) Date of Patent: Jun. 29, 2010

(54) METHOD FOR OBTAINING A PHARMACEUTICALLY ACTIVE COMPOUND, SYNTHESIS INTERMEDIATES THEREOF AND METHODS FOR OBTAINING THEM

(75) Inventors: Juan Antonio Perez Andres, Sant Feliu De Llobregat (ES); Pere Dalmases Barjoan, Sant Feliu De Llobregat (ES)

(73) Assignee: Inke, S.A., Castellbisbal (ES)

( * ) Notice: Subject to any disclaimer, the term of this patent is extended or adjusted under 35 U.S.C. 154(b) by 216 days.

(21) Appl. No.: 11/994,667

(22) PCT Filed: Jun. 26, 2006

(86) PCT No.: PCT/EP2006/063534
§ 371 (c)(1),
(2), (4) Date: Jan. 25, 2008

(87) PCT Pub. No.: WO2007/003522
PCT Pub. Date: Jan. 11, 2007

(65) Prior Publication Data
US 2008/0194824 A1    Aug. 14, 2008

(30) Foreign Application Priority Data
Jul. 6, 2005    (ES)    ................. 200501704

(51) Int. Cl.
*C07D 221/22*    (2006.01)
*C07D 451/00*    (2006.01)
*C07D 453/00*    (2006.01)
*C07D 455/00*    (2006.01)

(52) U.S. Cl. .......................................... 546/72; 546/94
(58) Field of Classification Search .................. 546/72, 546/94
See application file for complete search history.

(56) References Cited

U.S. PATENT DOCUMENTS 5,561,149 A    10/1996    Azria et al.

FOREIGN PATENT DOCUMENTS

| EP | 87116119.6 | | 5/1988 |
| EP | 89107764.6 | | 11/1989 |
| WO | 2006056081 | * | 6/2006 |
| WO | WO 2006/056081 A1 | | 6/2006 |

* cited by examiner

*Primary Examiner*—D. Margaret Seaman
*Assistant Examiner*—Niloofar Rahmani
(74) *Attorney, Agent, or Firm*—Cozen O'Connor

(57) ABSTRACT

The present invention relates to a method for obtaining Dolasetron that comprises: a) Esterification of the alcohol of formula (IV) with indole-3-carboxylic acid (compound (III)) or a reactive derivative thereof, to give a compound of formula (V), followed by step b) which includes Dieckmann reaction of the intermediate (V), by reaction with a strong organic or inorganic base, to give the intermediate (VI), and step c) which comprises dealcoxycarbonylation of the intermediate (VI) to give Dolasetron base and, if desired, a pharmaceutically acceptable salt thereof, hydrates or solvates of the base of said salt. The invention also relates to the intermediates (V) and (VI), and methods for obtaining them. With the method of the present invention Dolasetron is obtained at industrial scale with good yields, with decreased use of reactants and solvents, while said method is also of greater atomic efficiency.

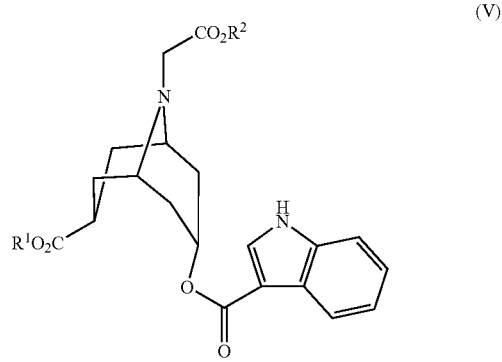

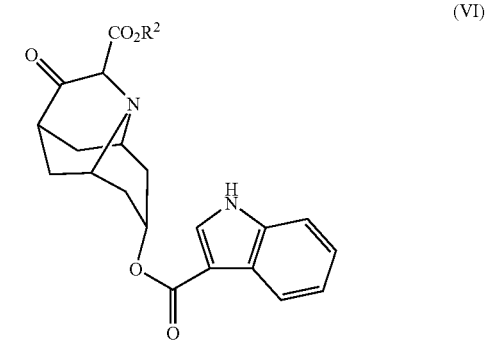

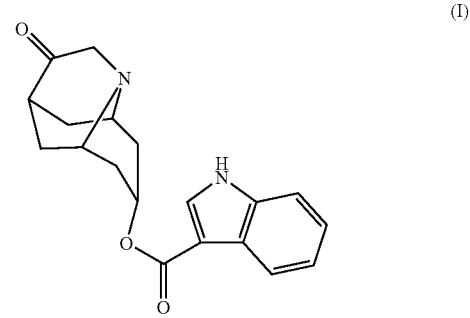

18 Claims, 3 Drawing Sheets

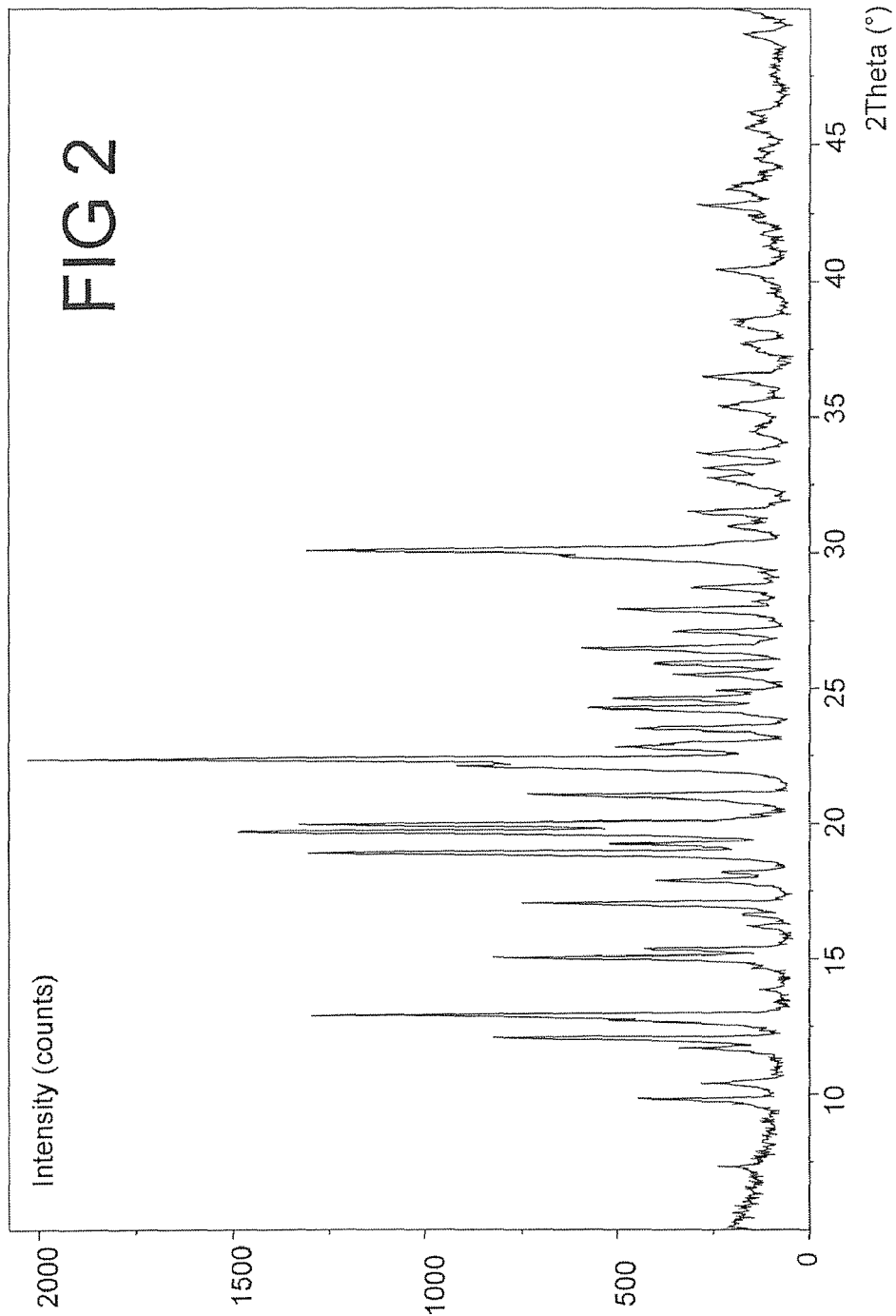

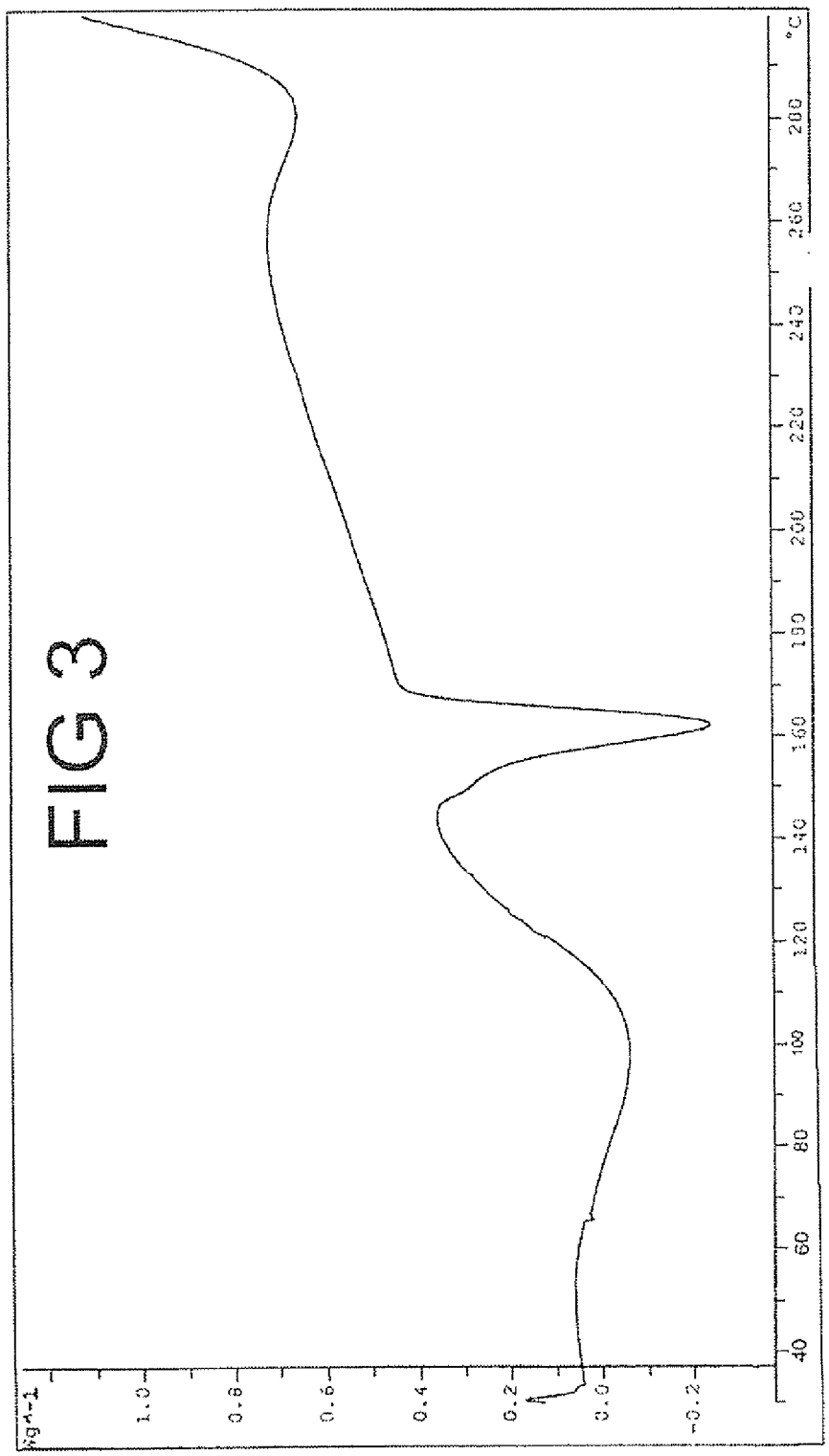

METHOD FOR OBTAINING A PHARMACEUTICALLY ACTIVE COMPOUND, SYNTHESIS INTERMEDIATES THEREOF AND METHODS FOR OBTAINING THEM

FIELD OF THE INVENTION

The present invention relates to a method for obtaining a pharmaceutically active compound with anti-emetic and anti-nausea properties, to its synthesis, intermediates and to the methods for obtaining them.

In particular, the present invention relates to a method that permits Dolasetron to be obtained at industrial scale and with good yields.

BACKGROUND OF THE INVENTION

European patent EP 339669 describes the preparation of Dolasetron I

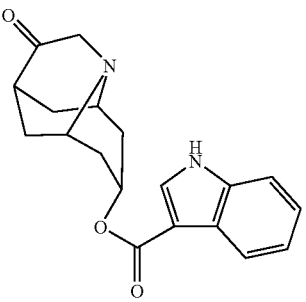

by means of a method that includes as its last step the reaction between the 5-hydroxy-8-azatricyclo[$5.3.1.0^{3,8}$]-undecan-10-one (compound II) and the mixed anhydride formed from indole-3-carboxylic acid (compound III) and trifluoroacetic anhydride:

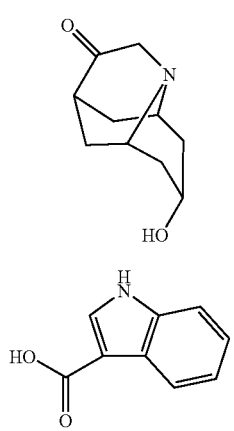

European patent EP 266730 (equivalent to Spanish patent ES 2061469) describes the preparation of compounds analogous to Dolasetron, also using the esterification described above as the last step.

These patents nevertheless present disadvantages. For example, in order to obtain compound II it is necessary to use protective groups that lengthen the synthesis route and entail a reduction of atomic efficiency. Moreover, the chosen protective group (Tetrahydropyranil, THP) leads to a mixture of diastereoisomers instead of to a single product. Also, the handling and purification of said intermediate product may prove to be complicated if carried out at industrial scale, as said mixture is an oil.

Another notable disadvantage is that column chromatography is used to carry out the purification of this mixture of diastereoisomers, while other methods of purification such as crystallisation or distillation are not possible. This becomes complicated if the product is to be prepared at industrial scale, and, combined with the atomic efficiency reduction remarked upon above, entails a considerable increase of residues and the attendant environmental problem.

Furthermore, the preparation of 5-hydroxy-8-azatricyclo [$5.3.1.0^{3,8}$]-undecan-10-one (compound II) includes a process of extraction of the product from the aqueous phase with ethyl acetate, in an operation that calls for the use of continuous-process extraction for considerable lengths of time (20 h), due to the high solubility of the compound in water. This operation requires specific installations which, although possible at industrial scale, means that the equipment needed to obtain the final product is more expensive.

Therefore, there remains a need for a method of obtaining Dolasetron which is applicable at an industrial scale, with fewer steps and which is more advantageous in terms of productivity, efficacy and minimisation of residues.

DESCRIPTION OF THE INVENTION

A first aspect of the present invention is to provide a method for obtaining Dolasetron at industrial scale, which gives good yields and has fewer steps.

The method defined in accordance with the first aspect of the invention overcomes the disadvantages of the prior art. Moreover, it is not necessary to use protective groups, which lengthen the synthesis of the method.

Advantageously, the method according to the first aspect of the invention is useful for carrying out at industrial scale, since it does not require specific installations. Similarly, this method presents the advantage that the synthesis intermediates are solid and therefore easily purifiable by recrystallisation, unlike the methods described in the prior art.

Also advantageously, it is carried out with decreased use of reactants and solvents and, still more advantageously, said method has greater atomic efficiency, since the proportion of atoms from the respective initial reagents that are incorporated into the final product is optimum and this translates itself into a reduction of the amounts of residues to be treated.

A second aspect of the invention is the synthesis intermediate defined by formula V.

A third aspect of the invention is the synthesis intermediate defined by formula VI.

A fourth aspect of the invention is to provide a method for obtaining the synthesis intermediate of formula V.

A fifth aspect of the invention is to provide a method for obtaining the synthesis intermediate of formula VI.

A sixth aspect of the invention is to provide a method for obtaining Dolasetron of formula I.

A seventh aspect of the invention is to provide a method for obtaining Dolasetron of formula I from the intermediate of formula V by means of two consecutive reactions that are carried out in a "one pot" procedure.

DEFINITIONS

In the present invention the term "aprotic organic solvent" is taken to mean a solvent that is not capable of exchanging protons with the reagents, such as those pertaining to the families of the aromatic hydrocarbons, amides, halogenated hydrocarbons, ketones, esters, ethers or sulphones. Preferably, benzene, toluene, xylene, dimethylformamide (DMF), dimethylacetamide, N-methylpyrrolidone, dichloromethane, chlorobenzene, chloroform, acetone, methylethylketone, cyclohexanone, Ethyl acetate, isopropyl acetate, diethylether, diisopropylether, 1,2-dimethoxyethane, dioxane, tetrahydrofuran (THF) or dimethylsulphoxide (DMSO) can be used.

The term "protic organic solvent" is taken to mean a solvent that is capable of exchanging protons with the reagents, such as those of the alcohol family. Preferably, MeOH, EtOH, $^i$PrOH or 1-propanol can be used.

The term "work up" is taken to mean the subsequent process of isolation and/or purification following the reaction, in which extractions or precipitations, for example, can take place in an aqueous or organic medium.

The term "one pot" is taken to mean a series of consecutive reactions that are carried out without isolating the respective intermediates.

The term "strong organic base" is taken to mean a base with a corresponding conjugated acid $pK_a$ greater than 16, from among those that have an alcoholate or amide as an anion and a metal of groups I and II as a cation. Also included are the organometallic compounds with group I and II metals. LDA, lithium hexamethyldisilazide, $^t$BuLi, MeONa, sodium tert-amylate or, more preferably, potassium tert-butoxide may be used.

The term "strong organic base" is taken to mean a base with a corresponding conjugated acid $pK_a$ greater than 16, among them being the hydrides of metals of groups I and II, preferably NaH.

The term "protective indole groups" is taken to mean any protective group of indoles described in "Protective groups in organic synthesis", T. W. Greene, P. G. M. Wuts, 3rd Ed. (1999), pages 615-631, such as the following: sulphonyl groups, preferably arylsulphonyl, and more preferably p-toluenesulphonyl; alcoxycarbonyl, preferably tert-butoxycarbonyl; or trialkylsilyl, preferably triisopropylsilyl or tert-butyldimethylsilyl.

DESCRIPTION OF THE FIGURES

FIG. 2 shows the X-ray diffraction pattern of the Dolasetron crystalline form obtained according to the method of the present invention.

FIG. 3 shows the DSC diagram of the Dolasetron crystalline form obtained according to the method of the present invention. (rate 10.0° C./min)

DETAILED DESCRIPTION OF THE INVENTION

Figure 1:
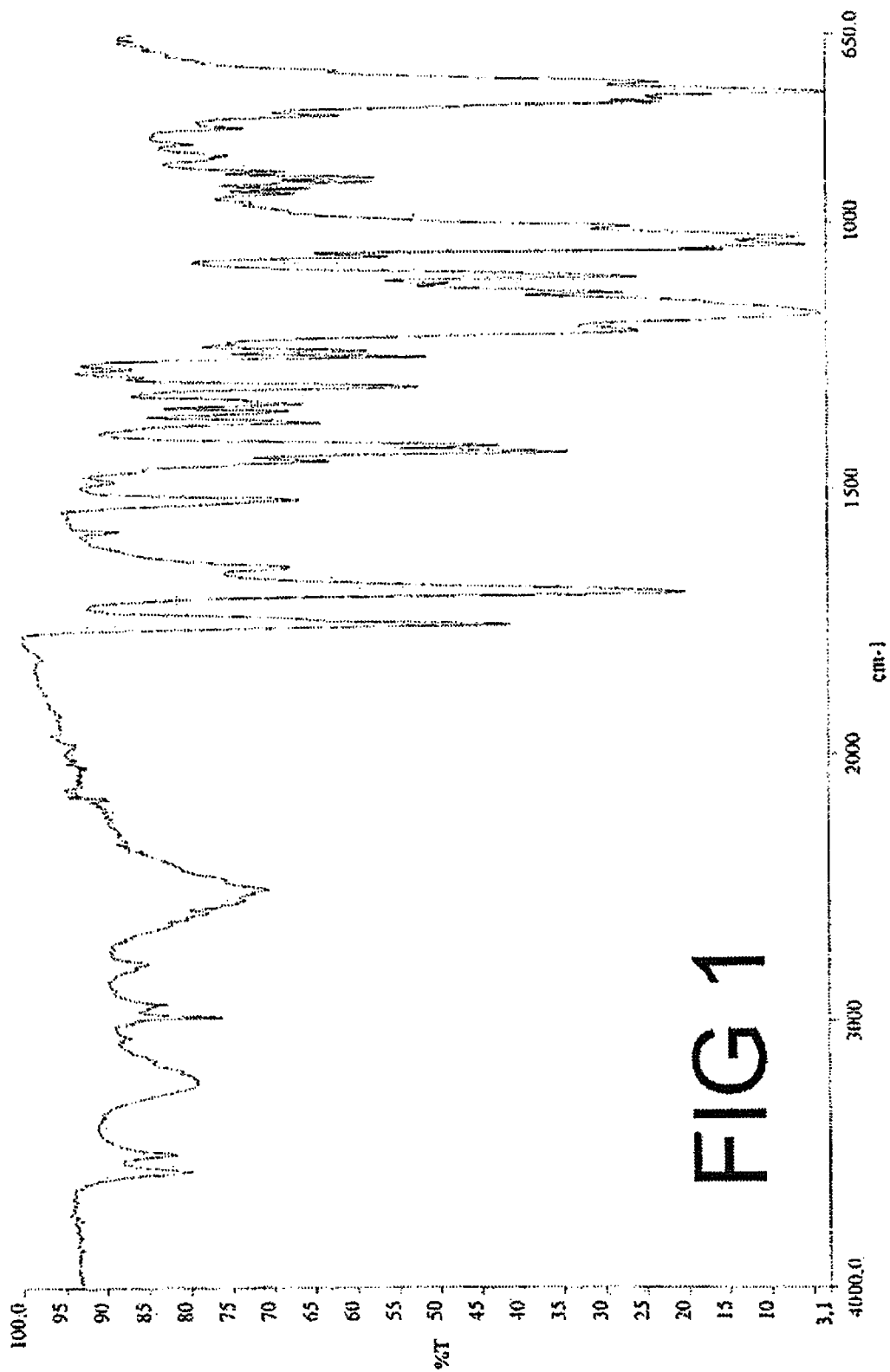
FIG. 1 shows the IR diagram (KBr) of the Dolasetron crystalline form obtained according to the method of the present invention.

The present invention has the object of providing a method for obtaining Dolasetron of formula (I), in accordance with the first aspect of the invention, which is characterised in that it comprises the following steps:

a) Esterification of the alcohol of formula IV with indole-3-carboxylic acid (compound III) or a reactive derivative thereof,

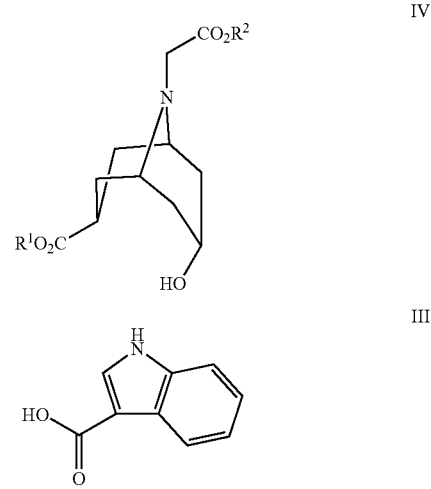

where $R^1$ and $R^2$ mean any linear or branched chain $C_1$-$C_4$ alkyl group, preferably methyl or ethyl, to give a compound of formula V:

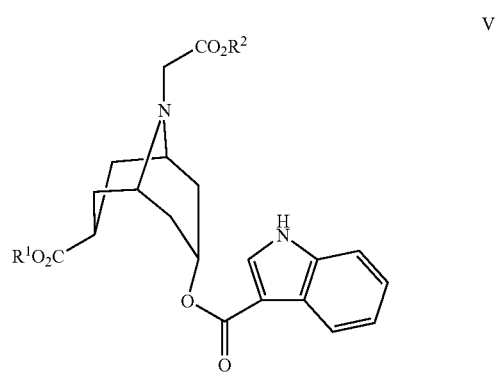

b) Dieckmann reaction of intermediate V, by reaction with a strong organic or inorganic base, to give intermediate VI:

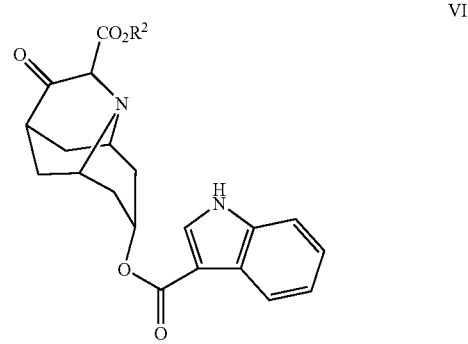

c) Dealcoxycarbonylation of intermediate VI to give Dolasetron base and, if required, a pharmaceutically acceptable salt thereof or hydrates or solvates of the base or of said salt.

Advantageously, with the method according to the first aspect of the invention it is not necessary to protect the indole group. The scope of the present invention nevertheless also includes incorporating protection and deprotection steps of the indole group, if desired.

Scheme I shows the complete sequence of steps:

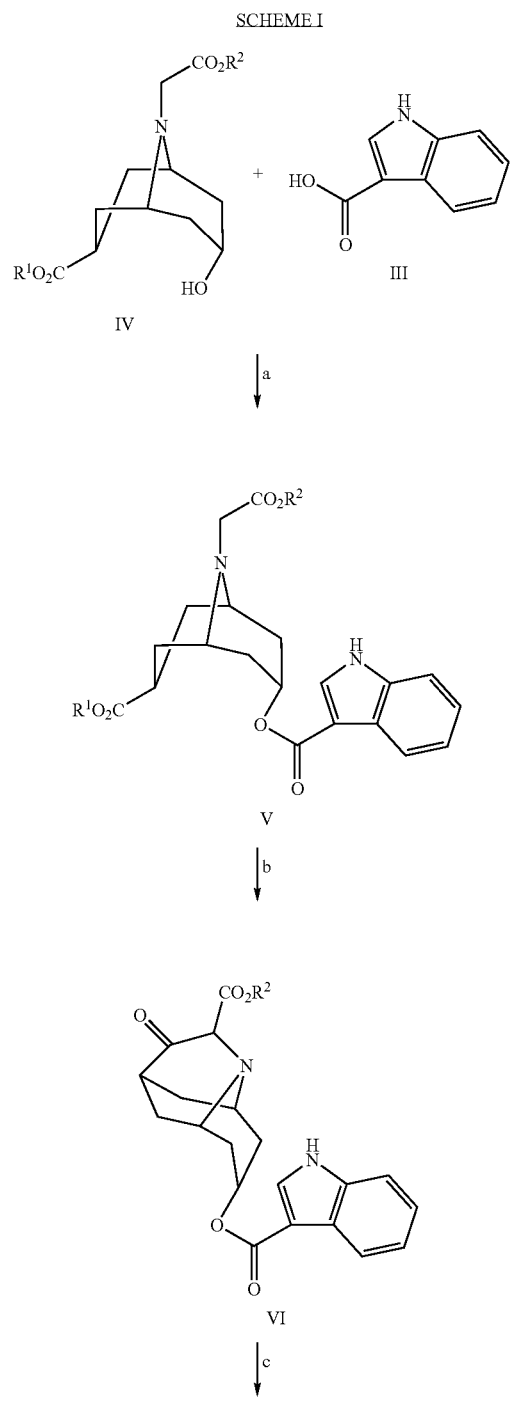

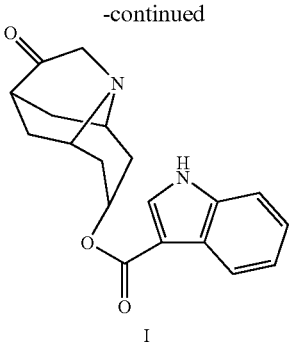

There follows below a more detailed description of each of the steps of this general method for obtaining Dolasetron:

Preparation of the Intermediate of Formula V (Step a) is carried out by treating the alcohol of formula IV, in which $R^1$ and $R^2$ mean any linear or branched chain $C_1$-$C_4$ alkyl group such as methyl, ethyl, propyl and butyl with linear chain, or for example branched-chain iso-Propyl, sec-Butyl, iso-Butyl and tert-Butyl, preferably methyl or ethyl, with indole-3-carboxylic acid (compound III) or a reactive derivative thereof, preferably that formed between said acid and the trifluoroacetic anhydride. The reaction takes place at a temperature between −50 and 100° C., preferably between −10 and 30° C. and more preferably between 0° C. and 25° C. The reaction is carried out in the presence of an aprotic organic solvent, such as dichloromethane, toluene or DMF, among others. The reaction can optionally be carried out in the presence of a catalyst, preferably DMAP (dimethylaminopyridine). The product is easily isolated by conventional methods.

The starting product for carrying out the method described above, the alcohol of formula IV, can be obtained, for example, by following the synthesis described in patent EP339669 A1 (Examples 1-4, pages 4-6).

Incorporation of the 3-carboxyindole group at this synthesis step permits the hydroxyl group of compound IV to be protected (necessary for carrying out step b) of the process). Highly advantageously, said group is not removed at the end of the synthesis, but instead forms an integral part of the final compound.

Step b) to obtain intermediate VI is carried out by treating the compound V with a strong organic or inorganic base, preferably potassium tert-butoxide in an aprotic organic solvent, preferably THF, at a temperature between −40° C. and 70° C., preferably between 0° C. and 25° C. The product can be isolated by conventional methods.

Dolasetron can be obtained from intermediate VI (step c) by applying one of the methods of dealcoxycarbonylation of 3-keto esters described in the bibliography and generally known to experts in the matter, preferably by treating with an inorganic salt such as LiCl, NaCl, NaBr, etc., and preferably with LiCl, in an aprotic organic polar solvent such as DMF, DMSO or N-methylpyrrolidone, at a temperature between 100° C. and 200° C., preferably between 130° C. and 150° C. The product is easily isolated by conventional methods.

Alternatively, and highly advantageously, steps b) and c) can be carried out as a one-pot reaction.

The Dolasetron base can, if wished, be converted subsequently into a pharmaceutically acceptable salt, or into hydrates or solvates thereof. By way of non-restrictive example, Dolasetron mesylate monohydrate can be prepared by treating Dolasetron base with methanesulphonic acid in an aprotic organic solvent, preferably acetone. The solid obtained can be recrystallised, for example, from a mixture of a protic organic solvent, preferably an alcohol, and more preferably still isopropanol, and water, to give Dolasetron mesylate monohydrate.

The solid thus obtained has a melting point between 160 and 163° C., with prior loss of the hydration water.

Dolasetron can thus be prepared by a more advantageous synthetic route than that described in the background of the invention. The number of steps is reduced from 4 to 3 (and eventually to 2 if steps b and c are carried out one-pot). Consequently, the amount of residues is reduced, particularly in relation to solvents, and the use of column chromatography (which consumes large amounts of solvent) is also avoided. There is also greater energy efficiency, since the times in each reaction are reduced, especially when it is considered that continuous extraction (20 h) is avoided.

The present invention also relates to synthesis intermediates useful for obtaining Dolasetron.

Thus, a second aspect of the present invention is the synthesis intermediate of formula V:

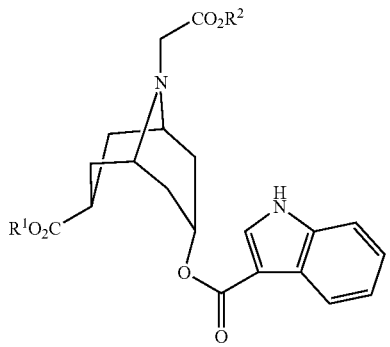

in which $R^1$ and $R^2$ mean any linear or branched chain $C_1$-$C_4$ alkyl group as defined above, preferably methyl or ethyl. It may later be protected by a protective group of indoles.

A third aspect of the invention is the synthesis intermediate of formula VI:

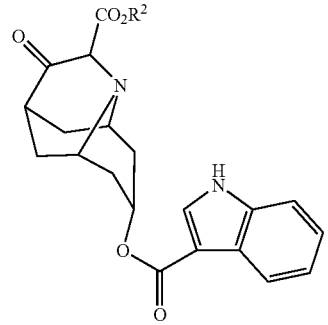

where $R^2$ means any linear or branched chain $C_1$-$C_4$ alkyl group as defined above, preferably methyl or ethyl. It may later be protected by a protective group of indoles.

Synthesis intermediates V and VI are useful for synthesising Dolasetron, although their use in the synthesis of other products also forms part of the scope of protection of the present invention.

Consequently, the steps described above in the method in accordance with the first aspect of the invention for obtaining Dolasetron can be considered independent methods for obtaining intermediate synthesis products, by isolating the intermediate product, where necessary.

Said steps are described below as independent aspects of the invention, used for obtaining each one of the synthesis intermediates.

Thus, a fourth aspect of the invention is the method for obtaining an intermediate of formula V by reaction between the alcohol of formula IV and indole-3-carboxylic acid (compound III) or a reactive derivative thereof.

A fifth aspect of the present invention is the method for obtaining the intermediate of formula VI, by reaction of the intermediate of formula V with a strong organic or inorganic base.

A sixth aspect of the present invention is to provide a method for obtaining Dolasetron, of formula I, by dealcoxycarbonylation of the intermediate of formula VI. This dealcoxycarbonylation can advantageously be carried out in an high boiling point (above 140° C.) organic solvent, such as DMF, DMSO or N-methylpyrrolidone, in the presence of an inorganic salt such as LiCl, NaCl or NaBr.

A seventh aspect of the invention is to provide a method for obtaining Dolasetron (I) from intermediate V, by consecutive one-pot Dieckmann reaction and dealcoxycarbonylation. Advantageously, with this method Dolasetron can be obtained in two steps from the alcohol of formula IV.

EXAMPLES OF SYNTHESIS

There follow some examples that show, by way of non-limited explanation of the invention, preferred embodiments of the various aspects thereof.

Example 1

Obtaining 7-(1H-Indole-3-carbonyloxy)-9-methoxy-carbonylmethyl-9-aza-bicyclo[3.3.1]nonane-3-carboxylic acid methyl ester Indole-3-carboxylic acid (6.43 gr, 39.9 mmol) is added in portions to a solution of 5.33 mL (37.7 mmol) of trifluoroacetic anhydride in dichloromethane (172 mL) and under nitrogen atmosphere. The resulting suspension is left under stirring for 30 minutes. 7-hydroxy-9-methoxycarbonylmethyl-9-aza-bicyclo[3.3.1]nonan-3-carboxylic acid methyl ester (6 gr, 22.1 mmol) dissolved in dichloromethane (15 mL) is then added dropwise. Next, a catalytic amount of DMAP is added, and the suspension is then left under stirring for 4 h. Following that time, and once the limiting starting product has been used up as shown by thin-layer chromatography (dichloromethane/methanol/ammonia 90:10:1, which reveals potassium permanganate), water (50 mL) is added to the reaction mixture and the mixture is basified with a saturated aqueous solution of sodium bicarbonate. Following filtration to remove the remains of indole-3-carboxylic acid in excess, the resulting phases are separated. The organic phase is dried over magnesium sulphate and evaporated to dryness, to give 7-(1H-Indole-3-carbonyloxy)-9-methoxycarbonylmethyl-9-aza-bicyclo[3.3.1]nonane-3-carboxylic acid methyl ester as a white solid (8.20 gr, 89%) that can be used directly in the following synthesis step.

NMR $^1$H (CD$_3$OD, 200 MHz) δ (ppm): 8.09-8.04 (m, 1H, Ar), 7.98 (s, 1H, Ar), 7.47-7.42 (m, 1H, Ar), 7.26-7.13 (m, 2H, Ar), 5.32 (m, 1H, CHOCO), 4.01-3.94 (s, 3H, CO$_2$CH$_3$), 3.72 (s, 3H, CO$_2$CH$_3$), 3.62 (s, 2H, CH$_2$CO$_2$Me), 3.53 (m, 1H, C HCO₂Me), 3.16 (m, 2H, (CH)₂N), 2.63-2.44 (m, 2H, carbocycle), 2.18-1.93 (m, 2H, carbocycle), 1.78-1.63 (m, 2H, carbocycle).

NMR $^{13}$C (CD₃OD, 50 MHz) δ (ppm): 178.3, 173.5 and 166.2 (C, CO₂), 138.1 (C, Ar), 133.1 (CH, Ar), 127.3 (C, Ar), 123.7 (CH, Ar), 122.5 (CH, Ar), 121.8 (CH, Ar), 112.9 (CH, Ar), 108.6 (C, Ar), 65.6 (CH, CH—OCOindole), 54.5 (CH₂, CH₂CO₂Me), 52.2 and 52.1 (CH₃, CO₂CH₃), 51.3 (CH, (CH)₂N), 34.0 (CH, CHCO₂Me), 32.5 and 29.0 (CH₂, carbocycle).

IR (KBr tablet, cm⁻¹): 3284, 2944, 1744, 1736, 1710, 1528, 1448, 1217, 1172, 1101, 1024, 751.

EM (mass spectrometry) (electrospray, positive): 415.3 (M⁺+1, 100).

R$_f$(AcOEt/MeOH 9/1)=0.55.

M.p.=152-155° C.

Example 2

Obtaining 5-(1H-Indole-3-carbonyloxy)-10-oxo-8-aza-tricyclo[5.3.1.0$^{3,8}$]undecane-9-carboxylic acid methyl ester 7-(1H-Indole-3-carbonyloxy)-9-methoxycarbonylmethyl-9-aza-bicyclo[3.3.1]nonane-3-carboxylic acid methyl ester (4.87 gr, 11.75 mmol) dissolved in THF (150 mL) is added to a mixture of potassium tert-butoxide (5.26 gr, 46.9 mmol) in THF (150 mL), under nitrogen. The resulting suspension is stirred for 3 h, until the starting product has been used up as shown by thin-layer chromatography (AcOEt/MeOH 9:1). When the reaction is considered completed, water is added and the pH adjusted to 7.5 with 1 M hydrochloric acid. The product is extracted with dichloromethane, and the organic phase is dried and evaporated, to provide 5-(1H-Indole-3-carbonyloxy)-10-oxo-8-aza-tricyclo[5.3.1.0$^{3,8}$]undecane-9-carboxylic acid methyl ester as a solid (3.63 gr, 81%).

NMR $^1$H (d6-DMSO, 200 MHz) δ (ppm): 11.90 (broad s, 1H, NH), 8.08-8.00 (m, 1H, Ar), 7.98 (s, 1H, Ar), 7.53-7.43 (m, 1H, Ar), 7.25-7.10 (m, 2H, Ar), 5.31 (m, 1H, CHOCOindole), 4.26 (s, 1H, CHCO₂Me), 3.68 (s, 3H, CO₂CH₃), 3.68-3.55 (m, 1H, CHCOCHCO₂Me), 2.50-2.35 (m, 4H), 2.21-2.04 (m, 4H).

NMR $^{13}$C (d6-DMSO, 50 MHz) δ (ppm): 213.6 (C, C—CO—C), 167.0 and 163.6 (C, CO₂), 136.6 (C, Ar), 132.3 (CH, Ar), 126.1 (C, Ar), 122.7 (CH, Ar), 121.5 (CH, Ar), 120.3 (CH, Ar), 112.6 (CH, Ar), 106.7 (C, Ar), 72.5 (CH, COCO), 65.7 (CH, CO—CH—CO₂Me), 52.3 (CH₃, CO₂CH₃), 48.7 and 44.1 (CH, (CH₂)₂CHN), 40.9 (CH, CHCOCHCO₂Me), 34.5, 34.1, 28.4 and 29.2 (CH₂, carbocycle).

IR (KBr tablet, cm⁻¹): 3328, 2951, 1749, 1729, 1699, 1583, 1528, 1434, 1310, 1171, 1028, 754.

EM (electrospray, positive): 383.4 (M⁺+1, 100).

R$_f$(AcOEt/MeOH 9/1)=0.20.

M.p.=197-204° C.

Example 3

Obtaining 1H-Indole-3-carboxylic acid 10-oxo-8-aza-tricyclo[5.3.1.0$^{3,8}$]undec-5-yl ester A mixture of 3.1 gr (8.1 mmol) of 5-(1H-Indole-3-carbonyloxy)-10-oxo-8-aza-tricyclo[5.3.1.0$^{3,8}$]undecane-9-carboxylic acid methyl ester and LiCl (0.69 gr, 16.23 mmol) in dimethylformamide (90 mL) is heated to 140° C. Once 4 hours have elapsed, and after checking by thin-layer chromatography (AcOEt/MeOH 9:1) that the reaction has been completed, the mixture is left to cool. Volatile substances are evaporated at low pressure and the residue is dissolved in dichloromethane (150 mL). This is washed with a saturated aqueous solution of NaCl (70 mL), and the organic phase is dried over magnesium sulphate and evaporated, to provide crude 1H-Indole-3-carboxylic acid 10-oxo-8-aza-tricyclo[5.3.1.0$^{3,8}$]undec-5-yl ester as a solid (2.18 gr, 83%).

NMR $^1$H (d6-DMSO, 200 MHz) δ (ppm): 11.90 (broad s, 1H, NH), 8.08-8.04 (m, 1H, Ar), 7.00 (s, 1H, Ar), 7.53-7.49 (m, 1H, Ar), 7.53-7.49 (m, 2H, Ar), 5.31 (broad s, 1H, CHOCOindole), 3.24 (s, 2H, CH₂CO), 3.24-3.18 (m, 2H, (CH)₂NCH₂CO), 2.50-2.33 (m, 3H, carbocycle), 2.12-1.95 (m, 6H, carbocycle).

NMR $^{13}$C (d6-DMSO, 50 MHz) δ (ppm): 219.8 (C, C—CO—C), 163.6 (C, CO₂), 136.6 (C, Ar), 132.2 (CH, Ar), 126.0 (C, Ar), 122.6 (CH, Ar), 121.5 (CH, Ar), 120.3 (CH, Ar), 112.6 (CH, Ar), 106.8 (C, Ar), 65.6 (CH, CHOCO), 63.0 (CH₂, N—CH₂—CO), 47.7 (CH, (CH)₂—N), 40.9 (CH, CHCO), 34.5 and 29.0 (CH₂, carbocycle).

IR (KBr tablet, cm⁻¹): 3251, 2896, 1717, 1698, 1529, 1444, 1310, 1184, 1126, 1106, 1064, 1034, 766, 776.

EM (electrospray, positive): 325.4 (M⁺+1, 100).

R$_f$(AcOEt/MeOH 9/1)=0.15.

M.p.: 213-216° C.

Example 4

Obtaining 1H-Indole-3-carboxylic acid 10-oxo-8-aza-tricyclo[5.3.1.0$^{3,8}$]undec-5-yl ester methanesulphonate monohydrate Methanesulphonic acid (0.34 mL, 5.24 mmol) is added to a solution of 1H-Indole-3-carboxylic acid 10-oxo-8-aza-tricyclo[5.3.1.0$^{3,8}$]undec-5-yl ester (1.6 gr, 4.93 mmol) in acetone (20 mL) and under nitrogen, maintaining the reaction temperature around 25° C. Following stirring at 0° C. for 3 h, and at room temperature for one night, the solid that forms is filtered and washed with acetone. The product formed is recrystallised from isopropanol-water (95:5 by weight), to obtain 1H-Indole-3-carboxylic acid 10-oxo-8-aza-tricyclo[5.3.1.0$^{3,8}$]undec-5-yl ester methanesulphonate monohydrate (1.71 gr, 79%) in the form of a white solid.

NMR $^1$H (d6-DMSO, 200 MHz) δ (ppm): 12.00 (broad s, 1H, NH), 10.39 (broad s, 1H, MsOH), 8.08-7.97 (m, 2H, Ar), 7.60-7.47 (m, 1H, Ar), 7.31-7.14 (m, 2H, Ar), 5.38 (broad s, 1H, CHOCOindole), 4.12 (s, 2H, CH₂CO), 4.02-3.90 (m, 2H, (CH)₂NCH₂CO), 2.63-2.50 (m, 3H, carbocycle), 2.38-2.22 (m, 9H, carbocycle).

NMR $^{13}$C (d6-DMSO, 50 MHz) δ (ppm): 204.6 (C, C—CO—C), 163.1 (C, CO₂), 136.7 (C, Ar), 132.7 (CH, Ar), 126.1 (C, Ar), 122.8 (CH, Ar), 121.7 (CH, Ar), 120.2 (CH, Ar), 112.7 (CH, Ar), 106.0 (C, Ar), 62.9 (CH, CHOCO), 59.2 (CH₂, CH₂CO), 49.9 (CH, (CH)₂NCH₂CO), 39.94 (CH, CHCO), 37.6 (CH₃SO₃), 31.9 and 25.4 (CH₂, carbocycle).

IR (KBr tablet, cm⁻¹): 3220, 2532, 1755, 1688, 1520, 1432, 1376, 1310, 1218, 1161, 1099, 1073, 1056, 777, 757.

M.p.: 160-163° C.

Karl-Fisher: 4.14% (theoretical monohydrate 4.11%).

The invention claimed is:

1. Method for obtaining a pharmaceutically active compound, Dolasetron, characterised in that it comprises the following steps:
   a) Esterification of the alcohol of formula IV with indole-3-carboxylic acid (compound III) or a reactive derivative thereof,

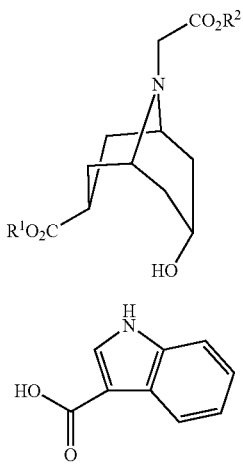

where $R^1$ and $R^2$ mean any linear or branched chain $C_1$-$C_4$ alkyl group, in which the indole group can optionally be protected with a protective group of indoles, to give a compound of formula V:

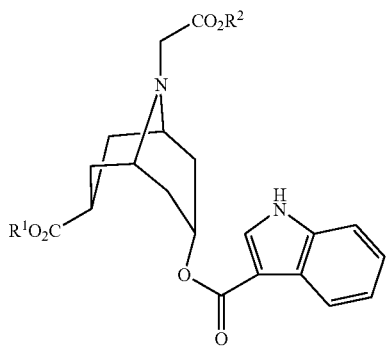

b) Dieckmann reaction of intermediate V, by reaction with a strong organic or inorganic base, to give the intermediate VI:

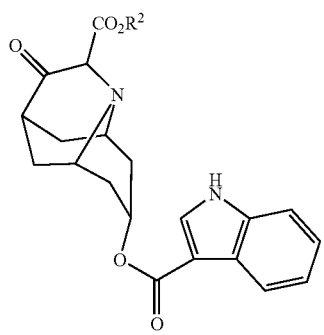

c) Dealcoxycarbonylation of the intermediate VI, and optionally deprotection of the indole group, to give Dolasetron base and, if desired, a pharmaceutically acceptable salt thereof, hydrates or solvates of the base or of said salt.

2. Method according to claim 1, characterised in that said indole protective group is selected from sulphonyl, alcoxycarbonyl or trialkylsilyl.

3. Method according to claim 1, characterised in that said reaction in step a) is carried out at a temperature between −50 and 100° C. and in the presence of an aprotic organic solvent.

4. Method according to claim 3, characterised in that said reaction is carried out between −10 and 30° C.

5. Method according to claim 4, characterised in that said reaction is carried out between 0° C. and 25° C.

6. Method according to claim 3, characterised in that said aprotic organic solvent is selected from dichloromethane, toluene and DMF.

7. Method according to claim 1, characterised in that said reaction in step a) is carried out in the presence of a catalyst.

8. Method according to claim 7, characterised in that said catalyst is DMAP.

9. Method according to claim 1, characterised in that said strong organic or inorganic base is potassium tert-butoxide.

10. Method according to claim 1, characterised in that said reaction in step b) is carried out at a temperature between −40° C. and 70° C., in an aprotic organic solvent.

11. Method according to claim 10, characterised in that it is carried out at a temperature between 0° C. and 25° C.

12. Method according to claim 10, characterised in that said aprotic organic solvent is THF.

13. Method according to claim 1, characterised in that the dealcoxycarbonylation of step c) is carried out by treating with an inorganic salt, in a polar aprotic organic solvent and at a temperature between 100° C. and 200° C.

14. Method according to claim 13, characterised in that it is carried out at a temperature between 130° C. and 150° C.

15. Method according to claim 13, characterised in that said inorganic salt is selected from LiCl, NaCl and NaBr.

16. Method according to claim 15, characterised in that said inorganic salt is LiCl.

17. Method according to claim 13, characterised in that said polar aprotic organic solvent has a high boiling point and is selected from DMF, DMSO or N-methylpyrrolidone.

18. Method according to claim 1, characterised in that steps b) and c) are carried out in a one-pot reaction.

* * * * *